United States Patent [19]

Nakano et al.

[11]  4,348,478

[45] * Sep. 7, 1982

[54] METHOD FOR PREPARATION OF A RECOMBINANT DNA PHAGE

[75] Inventors: Eiichi Nakano, Saitama; Tsutomu Masuda; Narimasa Saito, both of Noda, all of Japan; Danji Fukushima, Lake Jenova, Wis.

[73] Assignee: Noda Institute for Scientific Research, Noda, Japan

[ * ] Notice: The portion of the term of this patent subsequent to Sep. 7, 1999, has been disclaimed.

[21] Appl. No.: 87,167

[22] Filed: Oct. 22, 1979

[30] Foreign Application Priority Data

Oct. 25, 1978 [JP] Japan .................................. 53-130437

[51] Int. Cl.$^3$ .............................................. L12N 15/00
[52] U.S. Cl. ...................................... 435/172; 435/68; 435/235; 435/317
[58] Field of Search ................. 435/172, 68, 235, 238, 435/317

[56] References Cited

PUBLICATIONS

Murray et al., Nature, vol. 251, pp. 476–481, Oct. 1974.

Scott, Molecular Cloning of Recombinant DNA, pp. 133–153 (1977).
Levin, Gene Expression-3, pp. 269, 270, 879, 886 and 901, (1977).
Thomas et al., Proc. Nat. Acad. Sci. USA, vol. 71, No. 11, pp. 4579–4583 (1974).

*Primary Examiner*—Alvin E. Tanenholtz
*Attorney, Agent, or Firm*—Schuyler, Banner, Birch, McKie & Beckett

[57] ABSTRACT

A method for the preparation of a novel recombinant DNA, which comprises (1) cleaving with an endonuclease a temperate phage DNA having an endonuclease-sensitive region not in the DNA segment participating in the replication of phage DNA and the integration of phage DNA into a host chromosome but at least in the DNA segment carrying genetic information for the coat protein production and another DNA carrying intended genetic information, (2) adding DNA-ligase to the mixture of both cleft DNA's, and (3) recovering from the mixture a phage DNA having its coat protein producing ability deleted by the replacement of the DNA segments carrying genetic information for the coat protein production with a DNA fragment carrying the intended information.

13 Claims, No Drawings

METHOD FOR PREPARATION OF A RECOMBINANT DNA PHAGE

This invention relates to a method for the preparation of a novel recombinant DNA.

The genetic manipulation is a new research field initiated as the result of timely union between, on the one hand, the rapid progress in the researches on genetic and chemical properties of replicons such as plasmids and bacteriophages and, on the other hand, the progress in the researches on enzymes (restriction enzymes) associated with DNA (deoxyribonucleic acid), especially endonuclease which recognize the specific sequences of nucleotides in DNA and cause cleaving of polynucleotide chains and on DNA-ligase.

Various procedures have heretofore been proposed for the gene recombination. As an example, there is a known procedure for the recombination of a λ(lambda) phage DNA with a *Drosophila melanogaster* DNA fragment. However, since the site of recombination is the DNA segment carrying the genetic information necessary for lysogenization of the phage, it becomes impossible to integrate the resulting hybrid DNA into the host DNA. Consequently, in the actual case, it is necessary to preserve always the host cell and the phage for ready use, but the preservation of the phage presents a problem. In addition, when a plasmid having recombined genetic information for a specific enzyme protein infected the host, production of the specific enzyme will take place continually even when the host is in preserved state, thus causing considerable disturbance in host metabolism and inducing various secondary variations to compensate the disturbance. In actual cases, because of such secondary variations which profoundly affect the results, the genetic recombination procedure is far from being satisfactory.

In order to overcome the above difficulties, the present inventors conducted extensive researches by using a bacteriophage on the method for eliminating the endonuclease-sensitivity of the DNA segment participating in self-replication without impairing the self-replicative ability and for imparting endonuclease-sensitivity to the DNA segment participating in the coat protein production. As a result, it was found that by the hybridization between a phage having none of the endonuclease-sensitive regions and a phage of the same or related species having an endonuclease-sensitive region in the intended DNA segment or related segment it is possible to prepare easily and efficiently a self-replicative hybrid DNA molecule which retains endonuclease-sensitivity in the intended region and is self-replicative in cloning of gene in genetic manipulation. Based on this finding, the present invention has been accomplished.

An object this invention is to provide a method for preparing a novel recombinant DNA by replacing the DNA segment of a phage participating in the coat protein production by a DNA fragment carrying the intended genetic information to render the novel recombinant DNA to be able to produce a useful protein according to said intended genetic information or to produce a large quantity of the novel recombinant DNA itself.

Other objects and advantages of this invention will be apparent from the following descriptions.

According to this invention, there is provided a method for the preparation of a novel recombinant DNA, which comprises (1) cleaving with an endonuclease a temperate phage DNA having an endonuclease-sensitive region not in the DNA segment participating in the replication of phage DNA and the integration of phage DNA into a host chromosome but at least in the DNA segment carrying genetic information for the coat protein production and another DNA carrying an intended genetic information, (2) adding DNA-ligase to the mixture of both cleft DNA's and (3) recovering from the mixture a phage DNA having its coat protein producing ability deleted by the replacement of the DNA segments carrying genetic information for the coat protein production with a DNA fragment carrying the intended information.

The recombinant DNA obtained according to this invention can be integrated into a host chromosome and the recombinant DNA integrated into the host can be reproduced in a large amount by induction. Since the novel recombinant DNA is deleted of the coat protein producing ability, it cannot be transformed into an activated form and, accordingly, presents no pollution problem. Moreover, a DNA having a molecular weight higher than that of a conventional one can be used for the DNA carrying an intended genetic information.

The invention is described below in detail.

Although bacteriophage generally multiplies depending more or less on the function of its host, it is a replicon capable of multiplying independently of the host chromosome, namely, it is in the autonomous state. The bacteriophage used in this invention is a temperate phage having such a property that when the phage infected a host cell, its phage DNA can be integrated into the host cell DNA (lysogeny). Preferable temperate phages are lambdoid phages including λ(IFO 20016), 434(IFO 20018), 82(IFO 20019), φ80(IFO 20020), φ170(IFO 20021), etc. Also usable are those phage DNA's integrated into a host DNA such as, for example, φ80 lysogenized in coliform bacillus (*E. coli*) W3110 [*E. coli* K12 strain W3110 (φ80) (ATCC 31277)], λcI857 lysogenized in coliform bacillus (*E. coli*) W3350 [*E. coli* K12 strain W3350 (λcI 857) (ATCC 31278)], etc.

Preferred endonucleases are those of a high specificity capable of recognizing specific regions of the DNA chain and cleaving the DNA double helix at the recognized region so as to form "staggered" cohesive ends. Most suitable endonucleases are restriction enzymes including EcoRI, Bam I, and HindIII. The restriction enzymes are available from Seikagaku Kogyo Co. or Boehringer Mannhein Yamanouchi.

The bacteriophage used in this invention which has an endonuclease-sensitive region not in the DNA segment participating in the replication of DNA and integration of DNA into a host chromosome but at least in the DNA segment carrying genetic information for the coat protein production can be prepared by mating an endonuclease-resistant phage having in its DNA segment participating in the replication of DNA and integration of DNA into a host chromosome no region cleavable by endonuclease, such as an endonuclease-resistant phage uncleavable by a restriction enzyme (hereinafter such a phage is referred to simply as an endonuclease-resistant phage) with a phage having a region cleavable by an endonuclease at least in the DNA segment carrying genetic information for the coat protein production (hereinafter such a phage is referred to simply as an endonuclease-sensitive phage).

The endonuclease-resistant phage can be obtained in the following manner: Alternate cultivation of a lambdoid phage in a host containing a restriction enzyme and in another host containing no restriction enzyme results in extinction of a phage susceptible to the action of the restriction enzyme and gradual increase in the population of a mutant difficultly susceptible to said action. By such microbial concentration, it is possible to obtain finally a phage (restriction enzyme-resistant phage) containing DNA absolutely unsusceptible to the action of restriction enzyme (i.e. DNA whose chain is perfectly uncleavable by the action of a restriction enzyme).

The resistant phage can also be obtained more speedily by partially deleting the region cleavable by the restriction enzyme and then applying the microbial concentration technique. The method for partially eliminating the DNA region cleavable by restriction enzyme consists in isolating a deletion mutant in which the phage DNA segment including the cleavable region has been deleted. When the region cleavable by the restriction enzyme is located in a DNA segment unnecessary for the survival of the phage, the resistance of the phage against the restriction enzyme can be increased by isolating the mutant which is deleted of said segment. Owing to deletion of the DNA segment including the cleavable region, the deletion mutant has a reduced specific gravity and an improved thermal stability. By taking advantage of these properties, the mutant can be separated from an ordinary phage culture liquor, for example, by cesium chloride (CsCl) density-gradient centrifugation, whereby the separation is effected by centrifugation of the culture admixed with cesium chloride, or by heating the phage culture at about 60° C. and separating the survived phage. The separated mutant is subjected to microbial concentration by culturing the mutant alternately in a host having a restriction enzyme and an another host having no restriction enzyme. In such a manner, a phage having a DNA perfectly unsusceptible to the action of the restriction enzyme can be obtained more quickly.

When the endonuclease-resistant phage was obtained by microbial concentration after isolation of a deletion mutant, the deleted DNA segment contains a DNA segment participating in the integration of DNA into a host chromosome and if said segment is necessary, a phage having an endonuclease-resistant DNA segment participating in the replication of DNA and an endonuclease-sensitive DNA segment responsible for the integration of DNA into a host chromosome can be obtained by mating said endonuclease-resistant phage prepared from said deletion mutant with, for example, an immunity-variant of a parental strain used in the preparation of said deletion mutant. Examples of the said phage strains undergone immunity variation are those incapable of producing a protein necessary for immunity or those incapable of manifesting immunity owing to the variation in properties of the protein responsible for immunity or capable of manifesting immunity under specific conditions.

When the endonuclease-cleavage site of the deleted segment was not existed in the segment carrying the genetic information for the integration of DNA into a host, the obtained phage as such can be used as a phage resistant to endonuclease. If the endonuclease-cleavage site was existed in the segment carrying the genetic information for the incorporation of DNA into a host chromosome, the phage can be used as an endonuclease-resistant phage after eliminating completely the cleavable region by microbial concentration.

Next, in order to insert the region cleavable by the restriction enzyme into an intended segment of the phage obtained as described above, which is absolutely free from the site cleavable by the restriction enzyme, the phage is mated with a lambdoid phage having endonuclease sensitivity in the DNA segment carrying genetic information for the coat protein production. The mating is effected by mixing together two phage suspensions (each $10^9$–$10^{10}$/ml), the one resistant and the other sensitive to restriction enzyme, or infecting a coliform bacillus (in which both phages are multipliable) in the form of suspension ($10^8$–$10^9$/ml) with both phages, separately but successively or simultaneously as a mixture. The mating is also possible by inducing an endonuclease-resistant or -sensitive phage lysogenized in a coliform bacillus of the strain K12 and then infecting with another endonuclease-sensitive or -resistant phage. The coliform bacillus infected with the phage as above is cultured in a medium such as, for example, Tryptone medium (any medium can be freely used so long as growth of the bacillus is possible) by shaking at 37° C. for 1 to 2 hours.

The sensitive coliform bacillus suitable for use is any member of the strain K12 such as, for example, E. coli W3110 (ATCC 27325), E. coli W3350 (ATCC 27020), or E. coli 1100 (Max Planck Institute of F. R. Germany). The coliform bacillus can be used in the form of culture liquor or in the form of suspension prepared by centrifuging the culture to remove the supernatant, suspending the sediment in a magnesium chloride solution, and shaking for one hour at 37° C. The latter form is better for the adsorption and infection of the phage.

In the manner as described above, it is possible to obtain a phage having endonuclease-sensitivity only in the DNA segment carrying genetic information for the coat protein production.

The preparation of a novel phage $\lambda cI857RI'h80$ which is cleavable by the coliform bacillus restriction enzyme EcoRI only in the DNA segment carrying genetic information for the coat protein production is illustrated below with reference to Experimental Examples.

Experimental Example 1

1. Isolation of a deletion mutant phage $\lambda cI857b6042$ from phage $\lambda cI857$.

1-1. One platinum-loopful E. coli K12 strain W3350 ($\lambda cI857$; ATCC 31278) was inoculated into 3 ml of Tryptone medium and precultured by shaking for 16 hours at 30° C. The resulting preculture (3 ml) was mixed with 30 ml of Tryptone medium, cultured by shaking for 3 hours at 30° C., and then shaking for 20 minutes at 43° C. to induce phage $\lambda cI857$. The cultivation was continued for further 3 hours at 30° C. until bacteriolysis had taken place and the culture had become nearly transparent when the cultivation was discontinued. The culture liquor was centrifuged to remove cell fragments and obtain the supernatant as phage $\lambda cI857$ fluid (phage number $10^{11}$/ml).

1-2. A 0.1 ml portion of the phage $\lambda cI857$ fluid was suspended in 5 ml of Tris buffer solution (pH 8.2) containing 0.02 M ethylenediaminetetraacetic acid (EDTA), thereafter kept at 40° C. for 10 minutes and then diluted with 0.1 M Tris buffer solution (pH 7.2) containing 0.01 M magnesium chloride (hereinafter this solution is referred to as Tris-Mg buffer solution) to a final concentration of $10^7$/ml. A 0.1 ml portion of the diluted phage suspension and 0.25 ml of the culture of

*E. coli* W3110 (ATCC 27325) prepared by incubation at 37° C. for 16 hours in tryptone medium were spread together with 3 ml of molten $B_1$-soft agar, held at 46° C., over a Tryptone-agar plate and cultured at 37° C. for 4 hours. The phage on the plate was washed out with 4 ml of Tris-Mg buffer solution and preserved in a rubber-stoppered sterilized small test tube. Using a portion of this phage suspension, the same procedure as described above was repeated five times.

1-3. Using the phage obtained in 1-2, the same procedure as described in 1-2 was repeated four times, except that the treatment was carried out at 60° C. for 10 minutes in place of the treatment at 40° C. for 10 minutes. The resulting phage suspension was diluted with Tris-Mg buffer to $10^3$/ml. A 0.1 ml portion of the diluted phage suspension was mixed with 0.25 ml of the aforementioned culture of *E. coli* W3110, then spread over Tryptone-agar plate and cultured overnight at 37° C. The phage in one of the about 100 plaques on the plate was picked up with a bamboo spit and suspended in Tris-Mg buffer to obtain phage strain $\lambda$cI857b6042.

The deletion mutant thus obtained showed a specific gravity of 1.465, which was smaller than that of 1.493 of its parental strain $\lambda$cI857, and a deletion in DNA of about 23%, as calculated from the specific gravity. In DNA of the parental phage $\lambda$cI857, the number of cleavages caused by the restriction enzyme EcoRI (supplied by Seikagaku Kogyo Co.) was five, whereas the number was three in the case of the strain $\lambda$cI857b6042, as calculated from the number of survival determined by using *E. coli* W3110 and *E. coli* W3110(RI).

*E. coli* W3110(RI) had been isolated in the following manner. A mixture of *E. coli* RY-13 (supplied by H. W. Boyer of the University of California) having a drug-resistance factor RI (resistant to penicillin, streptomycin, tetracyclin and sulfamides) and *E. coli* W3110 (ATCC 27325) was cultivated and *E. coli* W3110(RI) having drug-resistance factor was isolated.

2. Isolation of the phage strain $\lambda$cI857b6042RI$^r$ absolutely resistant to the restriction enzyme EcoRI from the phage strain $\lambda$cI857b6042.

2-1. 0.25 ml of the overnight culture of *E. coli* W3110 obtained as in 1-2 and 0.1 ml of the phage $\lambda$cI857b6042 suspension were mixed together in 3 ml of molten $B_1$-soft agar held at 46° C. The resulting mixture was spread over Tryptone-agar plate and cultured at 37° C. for 4 hours. To the plate were then added 4 ml of Tris-Mg buffer solution and 3 drops of chloroform. The plate was left standing at 37° C. for 15 minutes and the supernatant was transferred by means of a pipette to a rubber-stoppered small test tube, the number of phage having been $6 \times 10^{10}$/ml.

2-2. The number of particles of the phage obtained in 2-1 was measured by using *E. coli* W3110(RI) containing the restriction enzyme EcoRI. [*E. coli* W3110(RI) cleaves and inactivates the phage DNA intruded into its cell by the action of its restriction enzyme. Consequently, the number of phage particles measured by using *E. coli* W3110(RI) is far smaller than that measured by using *E. coli* W3110 having no restriction enzyme, the former number having been $10^8$/ml which was 1/600 of the latter number.]

In the same manner as in 2-1, a phage suspension was prepared by using 0.25 ml of the culture liquor of *E. coli* W3110(RI) obtained by culturing as described in 1-2 and 0.1 ml of a phage suspension obtained by diluting the phage prepared in 2-1 to a phage concentration of $10^7$/ml, as measured by using the strain W3110(RI).

2-3. The phage obtained in 2-2 was treated by the procedure described in 2-1. In this way, the treatment was repeated ten times by using alternately the procedures of 2-1 and 2-2. The final treatment was carried out by using the procedure of 2-1. A sample of the finally obtained phage suspension showed substantially the same number of phage as measured by using either the strain W3110(RI) or the strain W3110, indicating that the phage sample consisted of a mutant strain absolutely resistant to EcoRI. This phage suspension was diluted to $10^3$/ml and 0.1 ml of the diluted suspension was mixed with 0.25 ml of the culture of the strain W3110. The resulting mixture was spread over the Tryptone-agar plate to form plaques not overlapping one another. From the plaques thus formed, a phage strain $\lambda$cI857b6042RI$^r$ absolutely resistant to EcoRI was isolated.

3. Formation of a phage containing a phage DNA having an endonuclease-sensitive region not in the DNA segment participating in the replication of temperate phage DNA and the integration of the DNA into a host chromosome but at least in the DNA segment carrying genetic information for the coat protein production from the phage $\lambda$cI857b6042RI$^r$ and the phage $\phi$80.

The DNA of the phage $\lambda$cI857 lacks by nature the region cleavable by EcoRI in the segment carrying the genetic information for the coat protein production. In order to impart a cleavable region to the said segment, EcoRI-resistant phage $\lambda$cI857b6042RI$^r$ was crossed with the phage $\phi$80, which is analogous to $\lambda$ phage, and a new phage $\lambda$cI857RI$^r$h80 was obtained in the following way.

One platinum-loopful *E. coli* W3110 was inoculated into 1 ml of Tryptone medium and cultured by shaking at 37° C. for 16 hours. A 0.1 ml portion of the culture was added to 15 ml of Tryptone medium and cultured by shaking at 37° C. until the number of cells had reached $3 \times 10^8$/ml, and then the culture liquor was centrifuged at 10,000 rpm for 10 minutes to collect the cells. The collected cells were suspended in 5 ml of Tris-Mg buffer solution, shaken for one hour at 37° C., and 0.2 ml of the resulting suspension was withdrawn into a test tube.

*E. coli* W3110 was cultured in Tryptone medium by shaking at 37° C. for 3 hours, then inoculated with $\lambda$cI857b6042RI$^r$ and cultured for further 4 hours. The culture liquor was then diluted 30-fold with Tris-Mg buffer solution to obtain a $\lambda$cI857b6042RI$^r$ suspension.

One platinum-loopful *E. coli* K12 strain W3110($\phi$80) (ATCC 31277) was inoculated into 3 ml of Tryptone medium and precultured by shaking at 37° C. for 16 hours. The 3 ml preculture thus obtained was added to 30 ml of Tryptone medium and cultured by shaking at 37° C. for 3 hours. A 15 ml portion of the culture was placed in a Petri dish, 15 cm in diameter, and irradiated with a 15 W ultraviolet lamp at a distance of 50 cm for 1 minute and thereafter again cultured by shaking at 37° C. for 4 hours. The resulting culture liquor was diluted 30-fold with Tris-Mg buffer to obtain a $\phi$80 suspension.

0.2 ml of the above $\lambda$cI857b6042RI$^r$ suspension ($3.4 \times 10^9$/ml) and 0.2 ml of the above $\phi$80 suspension ($3.3 \times 10^9$/ml) were added to 0.2 ml of a suspension of *E. coli* W3110 preserved in the test tube and the mixture was incubated at 37° C. for 10 minutes. Thereafter, 0.1 ml of the mixture was added to 10 ml of Tryptone medium and shaken for 70 minutes at 37° C. Then the culture was admixed with 7 drops of chloroform and shaken vigorously. 0.1 ml of the resulting mixture was mixed with E. coli W3110($\phi$80)/$\lambda$ ($\lambda$-resistant E. coli lysogenized with $\phi$80). 3 ml of B$_1$-soft agar held at 46° C. was added to the above mixture and spread over Tryptone-agar plate which was thereafter left standing overnight at 37° C. Phage particles were picked up by means of a bamboo spit from one of the plaques which were formed and suspended in Tris-Mg buffer solution. The plaque formation by using E. coli W3110-($\phi$80)/$\lambda$ was further repeated twice for the purpose of purification to obtain a novel phage $\lambda$cI857RI$^r$h80.

The above-noted E. coli W3110($\phi$80)/$\lambda$ had been obtained in the following manner.

One platinum-loopful E. coli K12 strain W3110($\phi$80) (ATCC 31277) was inoculated into 2 ml of Tryptone medium and incubated at 37° C. for 16 hours. A mixture composed of 0.1 ml of the culture and 0.1 ml of a $\lambda$v phage (IFO 20017) suspension was kept at 37° C. for 30 minutes. After adding 3 ml of B$_1$-soft agar held at 46° C., the mixture was spread over a Tryptone-agar plate and cultured at 37° C. for 48 hours. By using a platinum loop, the bacillus was picked out of one of the colonies on the plate and suspended in 5 ml of a sterilized 0.9% sodium chloride solution. 0.05 ml of this suspension was diluted 10,000-fold with the sterilized 0.9% sodium chloride solution. 0.1 ml of the diluted suspension was spread over Tryptone-agar plate and cultured at 37° C. for 48 hours. The bacillus was picked out of one of the colonies formed on the plate and was used as W3110($\phi$80)/$\lambda$.

The novel phage $\lambda$cI857RI$^r$h80 obtained as described above showed the following properties:

Host: The novel phage cannot infect a $\phi$80-resistant coliform bacillus but can infect a $\lambda$-resistant one. The host range is the same as that of phage $\phi$80 and different from that of phage $\lambda$, indicating that at least a part of the coat protein of the novel phage is identical with that of the phage $\phi$80.

Immunity: Immunity is the same as that of phage $\lambda$.

Restriction by EcoRI: The novel phage showed a value intermediate between those of both parental strains.

Temperature sensitivity: The novel phage $\lambda$cI857RI$^r$h80 cannot produce active phage particles at 43° C. This coincides with the fact that synthesis of the coat protein by phage $\phi$80 is impossible at 43° C., as contrasted to the case of phage $\lambda$.

The novel phage $\lambda$cI857RI$^r$h80 has been deposited in the American Type Culture Collection and assigned the ATCC number 31285.

In the next Experimental Example, are described the procedure of preparing a strain having an endonuclease-sensitive region only in the middle segment of an endonuclease-resistant phage by mating the endonuclease-resistant phage obtained from the deletion mutant with a wild-type strain; and the procedure of mating the strain thus obtained with a phage having an endonuclease-sensitive region in the DNA segment participating in the coat protein production.

Experimental Example 2

1-1. Mating of phage $\lambda$cI857b6042RI$^r$ with phage $\lambda$.

0.2 ml of the phage $\lambda$cI857b6042RI$^r$ suspension (3.6×10$^9$/ml) obtained in Experimental Example 1, 0.2 ml of a phage $\lambda$ suspension [3.5×10$^9$/ml; a suspension prepared by culturing E. coli W3110($\lambda$) (IFO 20016) in 15 ml of Tryptone medium while shaking at 37° C. until the number of bacillus reached 10$^9$/ml, then transferring the culture liquor into a Petri dish, 9 cm in diameter, exposing the culture liquor to a 15 W ultraviolet lamp at a distance of 50 cm for 2 minutes 12 seconds to induce multiplication of phage $\lambda$, and further culturing for 3 hours while shaking], and 0.2 ml of a suspension of E. coli 1100 (a suspension obtained by culturing E. coli 1100 in 15 ml of Tryptone medium while shaking until the number of bacillus reached 3×10$^8$/ml, collecting the cells by centrifuging, suspending the cells in 5 ml of Tris-Mg buffer, and shaking at 37° C. for 1 hour) were mixed and the mixture was left standing at 37° C. for 10 minutes. 0.1 ml of the resulting mixture was added to 10 ml of Tryptone medium and cultured by shaking at 37° C. for 100 minutes to obtain a phage culture liquor.

1-2. Fractionation of phage particles by cesium chloride (CsCl) density-gradient centrifugation.

The phage suspension prepared in 1-1 contained $\lambda$cI857b6042RI$^r$, $\lambda$, and their hybrids. In order to remove $\lambda$cI857b6042RI$^r$, the phage suspension was subjected to cesium chloride density-gradient centrifugation which is an effective means to separate high polymers of different specific gravity. Since $\lambda$cI857b6042RI$^r$ has lower specific gravity than that of $\lambda$, it can be removed by removing heavier pharge particles after centrifugation.

The phage suspension obtained in 1-1 was diluted 30-fold with Tris-Mg buffer. A 0.69 ml portion of the diluted suspension was placed in an ultracentrifuge tube (5 ml volume), admixed with 2.31 ml of a cesium chloride solution having a specific gravity of 1.6, then superposed with liquid paraffin and centrifuged in a swinging rotor at 25,000 rpm for 24 hours. Thereafter, a hole was drilled through the bottom of the tube so that the centrifuged suspension may be discharged drop by drop. Each 3 drops were successively collected in small test tubes. The phage was detected in the fractions contained in 11th to 14th and 16th to 20th test tubes. 0.1 ml of the fraction in the 12th test tube (containing a phage of higher specific gravity) was dialyzed with a cellulose tube successively against 1 M KCl, 0.3 M KCl and 0.1 M KCl aqueous solution. 0.05 ml of the dialyzed suspension was mixed with 0.1 ml of the E. coli 1100 suspension (2×10$^9$/ml), admixed with 3 ml of molten B$_1$-soft agar (46° C.), and spread over a Tryptone plate. When cultured overnight at 38° C., there appeared on the plate about 5,000 opaque plaques and 50 clear plaques. The phage forming opaque plaques is wild-type phage $\lambda$, while the phage forming clear plaques seemed to be a hybrid, because the latter phage has both properties of $\lambda$cI857b6042RI$^r$ (clear plaque) and wild-type $\lambda$ (higher specific gravity).

Phage particles were picked up with a bamboo spit from 12 clear plaques and suspended in 5 ml of Tris-Mg buffer and diluted 100-fold with the same buffer. 0.1 ml of the diluted suspension, 0.1 ml of E. coli 1100 suspension and 3 ml of molten B$_1$-soft agar (46° C.) were spread over a Tryptone-agar plate and cultured overnight at 38° C. to form plaques. This procedure was repeated once more and phage particles were picked up with a bamboo spit from the formed plaques. The phage particles were added to 0.1 ml of Tris-Mg buffer, admixed with 0.25 ml of the E. coli 1100 suspension (2×10$^9$/ml) and 3 ml of molten B$_1$-soft agar (46° C.) and spread over a Tryptone-agar plate. After culturing at 37° C. for 4 hours, 4 ml of Tris-Mg buffer and 3 drops of chloroform were added to the plate and left standing at 37° C. for 15 minutes. The supernatant was transferred by means of a pipet to a rubber-stoppered small test tube and preserved as a stock phage suspension.

By using E. coli 1100 and Tryptone medium, a large quantity of the phage were cultured and purified by means of the cesium chloride density-gradient centrifugation. The phage DNA was cleft by the restriction enzyme EcoRI of E. coli and examined by agarose gel electrophoresis. It was found that two of the 12 strains had two cleavage regions in the middle segment of DNA. One of such strains, $\lambda cI857sRI\lambda_3°sRI\lambda_2°sRI\lambda_1°$, was used in subsequent experiments.

2. Preparation of a temperate phage $\lambda cI857h80att\lambda$-$sRI\lambda_3°sRI\lambda_2°sRI\lambda_1°$ containing phage DNA having an endonuclease (restriction enzyme EcoRI)-sensitive region not in the DNA segment participating in the replication of DNA and the integration of DNA into a host chromosome but at least in the DNA segment carrying genetic information for the coat protein production from $\lambda cI857sRI\lambda_3°sRI\lambda_2°sRI\lambda_1°$ and $\phi 80ptrp$.

E. coli 1100 was cultured overnight in Tryptone medium at 37° C. 0.75 ml of the culture liquor was inoculated into 7.5 ml of Tryptone medium and cultured by shaking at 37° C. for 45 minutes. To the resulting culture liquor, was added 3.8 ml of a phage suspension prepared by mixing $\lambda cI857sRI\lambda_3°sRI\lambda_2°sRI\lambda_1°$ and $\phi 80ptrp$ (a transducing phage carrying genetic information for tryptophan synthetase of E. coli), diluting the mixture with Tris-Mg buffer to $1.1 \times 10^{10}$/ml for each phage, transferring the diluted mixture to a Petri dish, 9 cm in diameter, and exposing to a 15 W ultraviolet lamp at a distance of 50 cm for 2 minutes. The mixture was further shaken at 37° C. for 3 hours, then admixed with 5 drops of chloroform to prepare a lysate. 0.2 ml of the lysate thus obtained, 0.1 ml of E. coli W3110($\phi 80$)/$\lambda$ suspension ($10^9$/ml) and 3 ml of molten $B_1$-soft agar (46° C.) were spread over Tryptone-agar plate and cultured overnight at 37° C. Since E. coli W3110($\phi 80$)/$\lambda$ is a bacillus lysogenized with $\phi 80$, it does not support the growth of a phage having immunity of $\phi 80$; and, being $\lambda$-resistant, it is not infected with a phage having the coat protein of phage $\lambda$. Accordingly, the phage forming a plaque is $\lambda cI857h80$ which has the immunity of $\lambda$ and the coat protein of $\phi 80$. Five of the plaques (about 1200 in number) were picked up with a bamboo spit and each was purified twice on E. coli W3110($\phi 80$)/$\lambda$ and once on E. coli 1100, as described in 1-2, to prepare five stock suspensions. Each phage was cultivated in a large amount by using Tryptone medium and E. coli 1100. The culture liquor was concentrated by supercentrifuging and purified by cesium chloride density-gradient centrifugation. The DNA extracted from each phage was cleft with restriction enzyme EcoRI and examined by agarose gel electrophoresis. Two of the phages were found to be $\lambda cI857h80att\lambda sRI\lambda_3°sRI\lambda_2°sRI\lambda_1°$ having a region cleavable by restriction enzyme EcoRI not in the DNA segment participating in the replication of DNA and the integration of DNA into a host chromosome but in the DNA segment participating in the coat protein production and in the middle segment of the DNA molecule.

$\phi 80ptrp$ had been isolated in the following manner.

A coliform bacillus strain K12B$_4$ trp$^-$ (*a strain deleted of the ability to synthesize tryptophan synthetase; supplied by Stamford University, U.S.A.*) was inoculated into 15 ml of Tryptone medium, cultured by shaking at 37° C. for 4 hours, then centrifuged, and suspended in 15 ml of Tris-Mg buffer. To 1 ml of the suspension, was added 0.12 ml of a suspension ($2.2 \times 10^{10}$/ml; filtered through a membrane filter to remove bacteria) of phage $\phi 80$ [prepared by induction by ultraviolet rays from E. coli K12 strain W3110($\phi 80$) (ATCC 31277), a lysogen having tryptophan synthesizing ability]. After having been left standing at 37° C. for 15 minutes, each 0.1 ml of the resulting mixture was spread over a CA plate and cultured at 37° C. for 7 to 14 days. The bacterium cells were picked up with a bamboo spit from the colonies which were formed, then suspended in 4 ml of Tris-Mg buffer, admixed with 2 drops of chloroform and shaken vigorously. The resulting suspension was diluted 100-fold with Tris-Mg buffer. 0.05 ml of the diluted suspension was mixed with 0.1 ml of E. coli 1100 suspension ($2 \times 10^9$/ml), then admixed with 3 ml of molten $B_1$-soft agar (46° C.), and spread over a Tryptone-agar plate. After cultivating overnight at 37° C., the phage was picked up with a bamboo spit from the formed plaques and inoculated into an eM-SM plate which had been spread with 0.1 ml of a suspension ($10^9$/ml) of E. coli K12 B$_4$trp$^{-SMr}$ [a streptomycin resistant strain isolated from the colony grown on cultivating E. coli K12B$_4$trp$^-$ on an agar plate containing streptomycin] and 3 ml of 0.6% agar solution (46° C.). The plate was then incubated at 37° C. Since the eM-SM plate contained only a small amount of tryptophan which is necessary for the growth of E. coli K12B$_4$trp$^-$SM$^r$, only a small amount of bacterium cells grew on the plate. If the inoculant phage has tryptophan synthesizing ability, there is formed around the plaque a ring of said bacterium grown by utilizing tryptophan produced by the inoculant phage. Therefore, the phage producing such a ring was picked up with a bamboo spit and purified by the treatment described in 1-2 to obtain a phage stock suspension which was used in subsequent experiments as transducing phage $\phi 80ptrp$.

Note
(1) Tryptone-agar plate: 1% of Tryptone (Difco); 0.25% of sodium chloride; 1.2% of agar; after sterilization by autoclaving 30 ml was dispensed into each Petri dish, 9 cm in diameter.
(2) B$_1$-soft agar: 1% of Tryptone (Difco); 0.25% of sodium chloride; 5 mM of magnesium chloride; 1.5 $\mu$g/ml of vitamine B$_1$; 0.5% of agar; 3 ml was dispensed into each small test tube and sterilized by autoclaving.
(3) Tryptone medium: 1% of Tryptone (Difco); 0.25% of sodium chloride.
(4) CA plate: 0.7% of $K_2HPO_4$; 0.3% of $KH_2PO_4$; 0.05% of sodium citrate; 0.01% of $MgSO_4.7H_2O$; 0.1% of $(NH_4)_2SO_4$; 0.2% of glucose; 0.15% of casein hydrolysate; 1.5% of agar.
(5) eM-SM plate: 1.05% of $K_2HPO_4$; 0.45% of $KH_2PO_4$; 0.005% of $MgSO_4.7H_2O$; 0.1% of $(NH_4)_2SO_4$; 0.047% of sodium citrate; 0.2% of glucose; 0.01% of Difco nutrient broth; 0.01% of streptomycin sulfate; 1.5% of agar.

On the other hand, the DNA (donor DNA) carrying an intended genetic information is that orginated from microorganisms (bacteria, molds, yeasts), higher animals and plants, transducing phages, or the like. Examples of genetic information to be incorporated into the novel recombinant DNA include cystine synthetase, suppressor gene, DNA ligase, tryptophan synthetase, gene participating in the synthesis of silkworm fibroin, gene participating in the hormone synthesis, etc. Further, DNA of a transducing phage prepared by integrating the intended genetic information into an endonuclease-sensitive phage can also be used as the donor DNA.

In cleaving a phage DNA having an endonuclease-sensitive region not in the DNA segment participating in the replication of phage DNA and the integration of phage DNA into a host chromosome but at least in the DNA segment carrying genetic information for the coat protein production or cleaving a DNA carrying intended genetic information, it is suitable to allow the endonuclease to act at a DNA concentration of 20 to 200 μg/ml, an enzyme concentration of 100 to 2,000 units/ml and at a temperature of 26° to 42° C., preferably 37° C., for 10 minutes to 2 hours. The cleaving can be effected in a mixture of a phage DNA and a DNA carrying the intended genetic information.

Next, DNA-ligase is added to a mixture of generally equal amounts (in terms of DNA) of each suspension which has been subjected to the action of endonuclease. The DNA-ligase for use can be E. coli DNA ligase, T4 phage DNA-ligase, or the like. Of these, T4 phage DNA-ligase is most easily available. The DNA-ligase is allowed to act generally at a DNA concentration of 10 to 80 μg/ml, a DNA-ligase concentration of 1 to 10 units/ml, and at a temperature of 0° to 10° C. for 1 to 14 days.

The recovery of the intended recombinant DNA from the obtained mixture of various recombinant DNA's and other substances is performed in the following way:

At first, E. coli is lysogenized with a temperate phage having the same cohesive ends and immunity as those of the phage used in preparing the recombinant DNA but having a different attachment site (the region susceptible to recombination with a host chromosome in lysogenization). The resulting bacillus is infected with a large amount of a temperate phage having the same cohesive ends and immunity as those of the above-noted phage but having no attachment site to the host chromosome. The infected bacillus is mixed with the recombinant DNA and kept at 20° to 40° C. to allow the latter to be incorporated into the bacillus cell. Since the phage having the same immunity as that of the recombinant DNA has already been incorporated into the host, the recombinant DNA entered the cell cannot multiply and becomes readily integrated into the host chromosome.

When the donor DNA used for the recombination was originated from yeasts, bacteria, transducing phages, or the like, the differentiation of the cells containing the intended DNA among the cells lysogenized with the recombinant DNA as described above can be effected by collecting the cells producing the intended gene products. For instance, if the intended gene is a gene of tryptophan synthetase, the recombinant DNA is allowed to be incorporated into E. coli cells incapable of synthesizing tryptophane and the cells which restored the tryptophan synthesizing ability, that is, the cells capable of growing in a medium lacking tryptophan are collected.

When the donor DNA is originated from molds or higher organisms, it is used after having been combined, by means of DNA-ligase, with a gene capable of expression within E. coli cells, such as, for example, a fragment of plasmid DNA having a drug-resistant gene. The isolation of the intended recombinant DNA can be achieved by collecting the cells manifesting the genetic information for drug resistance.

It becomes necessary to ascertain whether or not the intended genetic information is incorporated to a phage DNA used as a vector (a DNA which can be combined with a donor DNA and used to prepare a recombinant DNA capable of autonomous replication) in place of the vector DNA segment participating in the synthesis of coat proteins. This can be achieved by mass-infecting the E. coli cells capable of producing the products of intended gene with a phage (e.g. phage C) having the same attachment site as that of the vector phage but having different immunity, isolating the cells lysogenized with said phage C, and examining whether or not these cells can produce the intended gene products. If the DNA fragment carrying the intended genetic information is bound to the vector phage DNA by replacing the DNA segment participating in the coat protein production and thus lysogenized in the host, the recombinant DNA is expelled from the host chromosome by the lysogenization of phage C; and as the host multiplies continually, the recombinant DNA in the host becomes progressively diluted until completely disappeared and becomes incapable of producing the products of intended gene.

The recombinant DNA is recovered in the following way from the cells in which the recombinant DNA is lysogenized, in the recombinant DNA, the DNA fragment carrying the intended genetic information having been recombined in place of the DNA segment participating in the coat protein production on the phage DNA molecule used as vector.

Since the host cell contains, in addition to the recombinant DNA, another phage DNA (the temperate phage DNA having the same attachment site and immunity as those of the phage used for the production of recombinant DNA and having a different attachment site) previously lysogenized in the cell, the latter phage DNA must be removed. For this purpose, when there is no great difference in molecular weight between the recombinant DNA and the previously lysogenized phage DNA, multiplication of both DNA's is induced at the same time and cultivation is continued. The recombinant DNA becomes packed in the coat protein produced according to the genetic information from the previously lysogenized phage DNA, forming infective phage particles. Accordingly, the lyzate contains both the previously lysogenized phage and the recombinant DNA. The lyzate is added to a suspension of non-lysogenic coliform bacillus to infect the bacillus and a large number of bacillus cells carrying the genetic information are separated as described above. From the cells thus separated, those not producing phage particles are collected. In order to find whether the phage particles are produced or not, a coliform bacillus capable of forming a plaque in the presence of the phage particles is spread over an agar plate and the sample cell being tested is spotted thereon. After incubation, occurrence or non-occurrence of lysis around the colony of sample cell is examined.

When the molecular weight of recombinant DNA differs greatly from that of previously lysogenized phage DNA, the host cell is mass-infected with another phage, which lysogenizes in the same region as that of the previously lysogenized phage but has different immunity and which cannot be induced to multiply by the same method as that applicable to the recombinant DNA, so that the previously lysogenized phage DNA may be replaced by the DNA of said another phage.

The cells thus treated are cultivated to induce replication of the recombinant DNA and immediately thereafter infected with a mutant phage (e.g. phage D) having the same cohesive ends as those of the recombinant DNA but having different molecular weight. On cultivation, the recombinant DNA is recovered as packed in coat protein produced by phage D. Since the resulting phage containing recombinant DNA has the same coat protein as that of phage D but has different molecular weight and, hence, different specific gravity, separation can be effected by the cesium chloride density-gradient equilibrium centrifugation.

In case the recombinant DNA has too large a molecular weight to be packed in the coat protein of phage D, the cells lysogenized with the combinant DNA are cultivated to induce replication of the recombinant DNA and the cultivation is continued to produce a great number of recombinant DNA in the cells. When DNA is extracted from the cells, DNA of the host bacterium having an extremely large molecular weight is cleft during the extraction and recovered as linear DNA fragments having both ends, while the recombinant DNA is recovered as a ring molecule with both ends joined together. The linear DNA and the ring DNA can be separated by the cesium chloride-ethidium bromide density-gradient equilibrium centrifugation and the recombinant DNA is thus isolated.

The novel recombinant DNA thus prepared by deleting the phage DNA segment carrying genetic information for the coat protein production and recombining with the DNA fragment carrying the intended genetic information can be preserved by infecting host cells and integrating into the host DNA. When required, the recombinant DNA preserved in host cells can be induced to "amplify" the genetic information. By culturing the host cells, for example, in Tryptone medium, a large amount of specific protein can be produced in accordance with the "amplified" genetic information. Thus, the industrial usefulness of this invention is believed to be very great.

The invention is illustrated below with reference to Example, but the invention is not limited thereto.

The media used in Example are as shown below.
(1) H-trp medium: A liquid medium containing 0.1 M potassium phosphate buffer (pH 7.0), 0.015 M $(NH_4)_2SO_4$, 1 mM of $MgSO_4$, $1.8 \times 10^{-6}$ M of $FeSO_4$, 0.2% of glucose, and 0.1 mg/ml of tryptophan.
(2) I-trp medium: A liquid medium containing 0.01 M of Tris buffer (pH 7.1), $6 \times 10^{-5}$ M of $MgCl_2$, $6 \times 10^{-4}$ M of potassium phosphate buffer (pH 7.1), $5 \times 10^{-4}$ M of $(NH_4)_2SO_4$, $4 \times 10^{-10}$ M of $FeSO_4$, 0.2% of glucose, and 0.1 mg/ml of tryptophan.

Example

1. Formation of recombinant DNA from $\lambda cI857h80att^\lambda sRI\lambda_3°sRI\lambda_2°sRI\lambda_1°$ DNA and $\phi 80ptrp$ DNA.

1-1. Cleaving of DNA with restriction enzyme EcoRI.

Each of the purified phages $\lambda cI857h80att^\lambda sRI\lambda_3°sRI\lambda_2°sRI\lambda_1°$ and $\phi 80ptrp$ [a transducing phage prepared by introducing the intended genetic information (tryptophan synthetase) into $\phi 80$] obtained in Experimental Example 2 was diluted with a buffer solution containing 0.01 M Tris-HCl (pH 8.0), 1 mM $MgCl_2$, and 0.1 mM ethylenediaminetetraacetic acid so that the absorbance at 260 m$\mu$ may become 8. 0.5 ml of the diluted phage suspension was dialyzed with a cellulose tube at 24° C. for 16 hours against 100 ml of 0.1 M Tris buffer (pH 8.5) containing 50% formamide and 10 mM ethylenediaminetetraacetic acid to extract DNA. The DNA extract was further dialyzed four times at 4° C. against 150 ml of 0.1 M Tris buffer solution (pH 7.5) containing 0.1 mM ethylenediaminetetraacetic acid to obtain standard samples of each DNA.

Each DNA sample was diluted with 0.1 M Tris buffer (pH 7.5) containing 0.1 mM ethylenediaminetetraacetic acid so that the concentration may become 40 $\mu$g/ml. 90 $\mu$l of the diluted DNA suspension was placed in a small test tube, admixed with 10 $\mu$l of 0.1 M magnesium chloride and 2 $\mu$l of restriction enzyme EcoRI (produced by Miles Lab. and supplied by Seikagaku Kogyo Co.), and left standing at 37° C. for one hour to effect cleaving of DNA. Thereafter, the cleft DNA was heated at 73° C. for 10 minutes and quickly cooled to 0° C. to inactivate EcoRI.

1-2. Formation of recombination DNA.

Each 25 $\mu$l of $\lambda cI857h80att^\lambda sRI\lambda_3°sRI\lambda_2°sRI\lambda_1°$ DNA and $\phi 80ptrp$ DNA, both cleft with the restriction enzyme, were mixed. After adding 20 $\mu$l of distilled water, 10 $\mu$l of 50 mM magnesium chloride, 10 $\mu$l of 0.1 M dithiothreitol, 10 $\mu$l of 1 mM ATP and 1 $\mu$l of $T_4$ ligase (produced by Miles Lab. and supplied by Seikagaku Kogyo Co.), the mixture was left standing for 3 days at 0° C. to obtain a liquor containing a recombinant DNA.

$T_4$ ligase is an enzyme having a function of uniting DNA fragments. Therefore, it is possible to prepare a recombinant by the action of this enzyme from two kinds of DNA cleft with a restriction enzyme.

2. Isolation of recombinant DNA.

E. coli K12B$_4$trp$^-$($\lambda cI857RI'h80$), which is a strain derived from E. coli K12B$_4$trp$^-$, a tryptophan-requiring strain, by lysogenization with $\lambda cI857RI'h80$ (ATCC 31285), was inoculated into 10 ml of H-trp medium and precultured at 30° C. for 20 hours. 0.5 ml of the preculture was inoculated into 10 ml of fresh H-trp medium and cultured by shaking at 30° C. When the number of cells had reached $5 \times 10^8$/ml, the culture liquor was cooled in ice. 6 ml of the cooled culture liquor was centrifuged (10,000 rpm, 20 minutes) and the cells were suspended in 1.5 ml of I-trp medium (0° C.). The resulting suspension was kept at 30° C. for 12 minutes and then at 0° C. for 6 minutes. To the suspension was added 1.5 ml of a suspension ($2 \times 10^{10}$/ml) of phage $\lambda b2$ (a phage having no attachment site to a host chromosome; supplied by National Institute of Health, Japan) in I-trp medium. After culturing at 30° C. for 12 minutes, the mixture was cooled to 0° C., then centrifuged and again suspended in 1.5 ml of 0.01 M Tris buffer (pH 7.5) containing 0.01 M magnesium chloride and 0.01 M calcium chloride. Normal E. coli cannot incorporate the external DNA into the cell, whereas when treated as described above, it becomes possible to incorporate a lambdoid phage DNA into the cell.

The liquor containing recombinant DNA formed in 1-2 was heated at 73° C. for 10 minutes and quenched. 5 to 20 $\mu$l of the cooled liquor was added to 0.1 ml of 0.01 M Tris buffer (pH 7.5) containing 0.01 M magnesium chloride and 0.01 M calcium chloride. To the resulting mixture, kept at 0° C., was added 0.2 ml of a suspension of E. coli K12B$_4$trp$^-$($\lambda cI857RI'h80$), which had been treated as described above. The mixture was kept at 30° C. for 40 minutes to incorporate the recombinant DNA into the bacterial cell. After addition of 3 ml of CA-soft agar (same composition as that of CA plate, except that the agar content was 0.5%), the mixture was spread over CA plate. After incubation for 3 days at 30° C., there were obtained 30 colonies. From the 30 colonies, those which showed no lysis in peripherial zone were separated. From the separated colonies, three bacterial strains showing no growth on a CA plate when precultured on a Tryptone-agar plate at 42° C. were isolated.

The three strains obtained above were tryptophan-nonrequiring, but when the lysogenized phage was removed by cultivating at 42° C., they become tryptophan-requiring. Therefore, these strains were *E. coli* K12B$_4$trp$^-$($\lambda$cI857RI$^r$h80, $\lambda$cI857h80watt$^\lambda$sRI$\lambda_3°$-sRI$\lambda_2°$sRI$\lambda_1°$ dtrp) which is a tryptophan-nonrequiring strain derived from K12B$_4$trp$^-$ (used as host) by the integration, into host DNA, of a DNA formed by recombination between a DNA fragment having all of the genetic information of $\lambda$cI857h80att$^\lambda$sRI$\lambda_3°$sRI$\lambda_2°$sRI$\lambda_1°$ DNA except for that coding for the coat protein synthesis and another DNA fragment involving a tryptophan operon derived from $\phi$80ptrp, that is, the novel recombinant DNA formed by replacing the DNA segment of $\lambda$cI857h80att$^\lambda$sRI$\lambda_3°$sRI$\lambda_2°$sRI$\lambda_1°$ DNA participating in the coat protein production with a DNA fragment participating in the synthesis of tryptophan synthetase.

What is claimed is:

1. A method for the preparation of a novel recombinant DNA, which comprises (1) cleaving with an endonuclease a temperate phage DNA having an endonuclease-sensitive region not in the DNA segment participating in the replication of phage DNA and the integration of phage DNA into a host chromosome but at least in the DNA segment carrying genetic information for the coat protein production and another DNA carrying intended genetic information, (2) adding DNA-ligase to the mixture of both cleft DNA's, and (3) recovering from the mixture a phage DNA having its coat protein producing ability deleted by the replacement of the DNA segment carrying genetic information for the coat protein production with a DNA fragment carrying the intended information.

2. A method according to claim 1, wherein the temperate phage is a lambdoid phage.

3. A method according to claim 2, wherein the lambdoid phage is lamda (IFO 20016) 434(IFO 20018), 82(IFO 20019), $\phi$80(IFO 20020), $\phi$170(IFO 20021), *E. coli* K12 strain W3110($\phi$80)(ATCC 31277) or *E. coli* K12 strain W3350($\lambda$cI857)(ATCC 31278).

4. A method according to claim 1, wherein the phage DNA having an endonuclease-sensitive region not in the DNA segment participating in temperate phage DNA replication and integration of DNA into a host chromosome but at least in the DNA segment carrying genetic information for the coat protein production is a DNA obtained by mating an endonuclease-resistant temperate phage with a temperate phage having an endonuclease-sensitive region in the DNA segment participating in the production of a coat protein.

5. A method according to claim 4, wherein the endonuclease-resistant temperate phage is a phage obtained from a deletion mutant by microbial concentration technique.

6. A method according to claim 1, wherein the phage DNA having an endonuclease-sensitive region not in the DNA segment participating in phage DNA replication and integration of DNA into a host chromosome but at least in the DNA segment carrying genetic information for the coat protein production is a DNA obtained by mating a phage having an endonuclease-sensitive region only in the middle of phage DNA with a transducing phage.

7. A method according to claim 6, wherein the phage having an endonuclease-sensitive region only in the middle of phage DNA is one obtained by mating an endonuclease-resistant phage with the parent strain thereof.

8. A method according to claim 1, wherein the DNA carrying intended genetic information is a DNA originated from molds, higher organisms or transducing phages.

9. A method according to claim 1, wherein the endonuclease is a restriction enzyme.

10. A method according to claim 9, the restriction enzyme is EcoRI, BamI or HindIII.

11. A method according to claim 1, wherein the DNA ligase concentration is 1 to 10 units/ml to the DNA concentration of 10 to 80 μg/ml.

12. A method according to claim 1, wherein the DNA ligase is *E. coli* DNA ligase or T$_4$ phage DNA ligase.

13. A method according to claim 11, wherein the mixture is kept at 0° to 10° C. for 1 to 14 days.

* * * * *